(12) United States Patent
Vukos et al.

(10) Patent No.: US 8,317,767 B2
(45) Date of Patent: Nov. 27, 2012

(54) ABSORBENT ARTICLE FORMED WITH MICROLAYERED FILM

(75) Inventors: John P. Vukos, Neenah, WI (US); Vasily A. Topolkaraev, Appleton, WI (US); Thomas W. Odorzynski, Green Bay, WI (US); Palani Raj Ramaswami Wallajapet, Neenah, WI (US); Georgia L. Zehner, Larsen, WI (US); Duane G. Uitenbroek, Little Chute, WI (US); Richard W. Tanzer, Neenah, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 817 days.

(21) Appl. No.: 11/622,277

(22) Filed: Jan. 11, 2007

(65) Prior Publication Data

US 2007/0129698 A1 Jun. 7, 2007

Related U.S. Application Data

(62) Division of application No. 10/647,414, filed on Aug. 25, 2003, now Pat. No. 7,179,852.

(51) Int. Cl.
*A61F 13/15* (2006.01)
*A61F 13/20* (2006.01)
(52) U.S. Cl. .............................. 604/385.101
(58) Field of Classification Search .......... 604/385.101
See application file for complete search history.

(56) References Cited

U.S. PATENT DOCUMENTS

| | | | |
|---|---|---|---|
| 479,999 A | 8/1892 | Thompson | |
| 520,366 A | 5/1894 | Leaver | |
| 1,189,140 A | 6/1916 | Lane | |
| 2,091,918 A | 8/1937 | Finck | |
| 2,314,876 A | 3/1943 | Greene | |
| 3,051,453 A | 8/1962 | Sluijters | |
| 3,576,707 A | 4/1971 | Schrenk | |
| 4,076,663 A | 2/1978 | Masuda | |
| 4,286,006 A | 8/1981 | Boelter | |
| 4,286,082 A | 8/1981 | Tsubakimoto | |
| 4,323,069 A * | 4/1982 | Ahr et al. ...................... | 604/378 |
| 4,604,313 A | 8/1986 | McFarland | |
| 4,655,757 A | 4/1987 | McFarland | |
| 4,704,116 A | 11/1987 | Enloe | |
| 4,724,114 A | 2/1988 | McFarland | |
| 4,741,941 A | 5/1988 | Englebert | |
| 4,880,682 A | 11/1989 | Hazelton | |
| 4,940,464 A * | 7/1990 | Van Gompel et al. ........ | 604/396 |
| 4,990,147 A * | 2/1991 | Freeland .................. | 604/385.22 |

(Continued)

FOREIGN PATENT DOCUMENTS

EP 0 151 018 A2 8/1985

(Continued)

OTHER PUBLICATIONS

Schrenk, W.J. and T. Alfrey Jr., "Coextruded Multilayer Polymer Films and Sheets," Chapter 15, Polymer Blends, vol. 2, 1978, pp. 129-165.

(Continued)

*Primary Examiner* — Melanie Hand
(74) *Attorney, Agent, or Firm* — Armstrong Teasdale LLP

(57) ABSTRACT

An absorbent article includes a liquid intake region, a liquid retention region, a barrier region, and plural strips of microlayer material located adjacent to the liquid retention region.

9 Claims, 9 Drawing Sheets

U.S. PATENT DOCUMENTS

| | | | |
|---|---|---|---|
| 5,143,676 A | 9/1992 | Müller | |
| 5,143,679 A | 9/1992 | Weber | |
| 5,261,899 A | 11/1993 | Visscher | |
| 5,269,995 A | 12/1993 | Ramanathan | |
| 5,376,430 A | 12/1994 | Swenson | |
| 5,462,708 A | 10/1995 | Swenson | |
| 5,468,428 A | 11/1995 | Hanschen | |
| 5,486,167 A | 1/1996 | Dragoo | |
| 5,536,555 A | 7/1996 | Zelazoski | |
| 5,562,465 A | 10/1996 | Taguchi | |
| 5,562,650 A | 10/1996 | Everett | |
| 5,593,399 A | 1/1997 | Tanzer | |
| 5,645,929 A | 7/1997 | Debe | |
| 5,667,864 A | 9/1997 | Landoll | |
| 5,691,034 A | 11/1997 | Krueger | |
| 5,700,553 A | 12/1997 | Cohen | |
| 5,756,039 A | 5/1998 | McFall | |
| 5,773,562 A | 6/1998 | Gruber | |
| 5,800,758 A | 9/1998 | Topolkaraev | |
| 5,814,178 A | 9/1998 | Jacobs | |
| 5,843,063 A | 12/1998 | Anderson | |
| 5,866,173 A | 2/1999 | Reiter | |
| 5,873,963 A | 2/1999 | Trombetta | |
| 5,882,769 A | 3/1999 | McCormack | |
| 5,938,648 A | 8/1999 | La Von | |
| 5,944,706 A | 8/1999 | Palumbo | |
| 6,071,450 A | 6/2000 | Topolkaraev | |
| 6,107,538 A | 8/2000 | Young | |
| 6,117,438 A | 9/2000 | Topolkaraev | |
| 6,231,557 B1 | 5/2001 | Krautkramer | |
| 6,258,996 B1 | 7/2001 | Goldman | |
| 6,261,674 B1 | 7/2001 | Branham | |
| 6,383,960 B1 | 5/2002 | Everett | |
| 6,419,798 B1 | 7/2002 | Topolkaraev | |
| 6,459,514 B2 | 10/2002 | Gilbert | |
| 6,462,251 B1 | 10/2002 | Cimini | |
| 6,475,600 B1 | 11/2002 | Morman | |
| 6,492,574 B1 | 12/2002 | Chen et al. | |
| 6,500,159 B1 | 12/2002 | Carvalho | |
| 6,586,354 B1 | 7/2003 | Topolkaraev | |
| 6,642,428 B1 | 11/2003 | Kurata et al. | |
| 6,664,436 B2 | 12/2003 | Topolkaraev | |
| 6,764,566 B1 | 7/2004 | Griesbach, III | |
| 6,933,421 B2 | 8/2005 | Topolkaraev | |
| 6,967,261 B1 | 11/2005 | Soerens | |
| 2002/0019187 A1 | 2/2002 | Carroll | |
| 2002/0062113 A1* | 5/2002 | Thomas et al. | 604/378 |
| 2002/0127385 A1 | 9/2002 | Topolkaraev | |
| 2002/0165516 A1 | 11/2002 | Datta | |
| 2003/0031837 A1 | 2/2003 | Kody | |
| 2003/0100872 A1* | 5/2003 | Roe et al. | 604/361 |
| 2003/0125682 A1* | 7/2003 | Olson et al. | 604/361 |
| 2003/0144643 A1 | 7/2003 | Jarpenberg | |
| 2004/0089412 A1 | 5/2004 | Topolkaraev | |
| 2004/0091677 A1 | 5/2004 | Topolkaraev | |
| 2005/0027268 A1 | 2/2005 | Qin | |

FOREIGN PATENT DOCUMENTS

| | | |
|---|---|---|
| WO | 9933651 A1 | 7/1999 |
| WO | 0126597 A1 | 4/2001 |
| WO | 2004043695 A1 | 5/2004 |
| WO | 2006073554 A1 | 7/2006 |

OTHER PUBLICATIONS

Mueller et al., Breathable Polymer Films Produced by the Microlayer Coextrusion Process, Journal of Applied Polymer Science, 2000, pp. 816-828, vol. 78, No. 4, John Wiley and Sons, Inc., New York, USA.

International Search Report from PCT/US2004/017677 dated Oct. 18, 2004.

American Society for Testing Materials (ASTM) Designation: D1238-04c, "Standard Test Method for Melt Flow Rates of Thermoplastics by Extrusion Plastometer," pp. 1-14, published Dec. 2004.

Im, J. and W.J. Schrenk, "Coextruded Microlayer Film and Sheet," Journal of Plastic Film & Sheeting, vol. 4, Apr. 1988, pp. 104-115.

Mueller, Chad D. et al., "Novel Structures by Microlayer Coextrusion-Talc-Filled PP, PC/SAN, and HDPE/LLDPE," Polymer Engineering and Science, vol. 37, No. 2, Feb. 1997, pp. 355-362.

* cited by examiner

ABSORBENT ARTICLE FORMED WITH MICROLAYERED FILM

CROSS-REFERENCE TO RELATED APPLICATION

This patent application is a divisional application of U.S. patent application Ser. No. 10/647,414 filed on Aug. 25, 2003, which is incorporated herein by reference in its entirety.

FIELD OF THE INVENTION

This invention relates generally to microlayer film structures for personal care products and, more specifically, to a microlayered film system for carrying out the essential requisite functions of personal care products.

BACKGROUND OF INVENTION

Absorbent articles typically may take the form of diapers, children's training pants, adult incontinence items, feminine hygiene products, bandages and the like. Generally, all are capable of absorbing and retaining liquids, and particular body exudates, for maintaining the skin adjacent the absorbent article dry and protecting clothing or other items which may come near or into contact with the absorbent article. "Liquid", as used herein, includes urine and viscous body exudates such as menstrual fluid and loose feces. Usually these items are disposable, but may be constructed for washing and reuse.

The absorbent article is made by making and assembling several different components which have different functions. For instance in the case of a diaper or training pant, a bodyside liner is formed of a material which is comfortable when contacting the skin, but which also is highly fluid permeable and hydrophobic to maintain a dry surface in contact with the skin even after receiving multiple insults of urine. An uptake and distribution region is formed of a material that is capable of rapidly absorbing a surge of liquid passed through the bodyside liner to remove the liquid from the area of the skin. Usually the region also functions to distribute the liquid over a larger area within the region, but does not permanently retain the liquid. An absorbent core or retention region provided to retain the liquid is positioned adjacent to the uptake and distribution region so that liquid may pass out of that region into the retention region where it is held for the remainder of the time the diaper is in use. A barrier region defines the exterior of the diaper and is substantially liquid impermeable, but is desirably vapor permeable to enhance breathability of the diaper.

Conventionally, the various regions described are formed separately and then brought together at an assembly location. In addition to the regions, other components of a diaper (or other absorbent article) including waist and leg elastics, containment flaps and fasteners are brought together for assembly. One or more of the regions may be formed of several components which must be assembled. The retention region or absorbent core is most often formed by depositing absorbent fluff and superabsorbent material into a form which shapes the core. The bodyside liner, uptake and distribution region and barrier region may be formed from various known materials having the necessary functionality. Frequently, the materials of the aforementioned diaper components are quite different from each other. All of these various components are brought together into an assembly process to form the finished diaper. The manufacturer of the diaper must either make or purchase the various components and have suitable machinery to integrate them into the finished product.

It is known that polymer films are useful in making a variety of disposable absorbent articles because such films are relatively inexpensive to make and can be made to be strong, durable, flexible, soft and a barrier to liquids, such as water, blood and urine. For example, polymer films are used to make disposable personal care products such as diapers, adult incontinence items, feminine care absorbent products, children's training pants, bandages and the like. In particular, polymer films are suitable as outer covers for absorbent personal care products, and are also useful in making some types of garments and coverings for various articles. In the past various polymer films have been used as selected components in making absorbent articles, especially as covers for the cellulosic absorbent core. U.S. Pat. No. 6,117,438 entitled WATER DEGRADABLE MICROLAYER POLYMER FILM AND ARTICLES INCLUDING SAME, issued Sep. 12, 2002, discloses microlayer polymer films forming tiers of coextruded microlayer polymer laminates having both water degradable and non-degradable layers, and discloses a method of making such microlayer film laminates. U.S. Pat. No. 6,261,674 entitled BREATHABLE MICROLAYER POLYMER FILM AND ARTICLES INCLUDING SAME, issued Jul. 17, 2001, discloses a breathable microlayer film formed of coextruded microlayers of polymers useful for certain parts of absorbent articles. Microlayer polymer films and methods of making such films using a coextrusion system and process of splitting and stacking multiple microlayered films are disclosed in U.S. Pat. No. 6,071,450 issued Jun. 6, 2000 for METHOD FOR MAKING WATER DEGRADABLE POLYMER MICROLAYER FILM AND ARTICLES INCLUDING SAME. The disclosures of U.S. Pat. Nos. 6,071,450, 6,117,438 and 6,261,674 are incorporated herein by reference.

SUMMARY OF THE INVENTION

In one aspect, an absorbent article comprises a liquid intake region, a liquid retention region, a barrier region, and plural strips of microlayer material located adjacent to the liquid retention region.

In another aspect, a method of making an absorbent article comprises forming a first through fourth microlayer films, each including multiple microlayers. The first microlayer film is activated to form an intake function region. The second microlayer film is activated to form an uptake and distribution function region. The third microlayer film is activated to form a retention function region, and the fourth microlayer film is activated to form a barrier function region. The first, second, third and fourth microlayer films are assembled to form the absorbent article.

BRIEF DESCRIPTION OF THE DRAWINGS

Corresponding reference characters indicate corresponding parts throughout the several views of the drawings.

DETAILED DESCRIPTION OF THE INVENTION

The present invention is embodied in a unitary system of microlayered film having sufficient elasticity, strength and breathability for use in various applications of absorbent personal care products. Thus, the technology of the invention can be configured to produce various types of desired absorbent articles, such as infant diapers, children's training pants, feminine care articles, adult incontinence products, bandages and like health care articles for use in absorbing various body exudates. It is envisioned that the present invention also has application outside the health care field, such as for cleaning wipes not necessarily associated with personal care. The articles may be, but are not necessarily, disposable, and intended for limited use.

Figure 1:
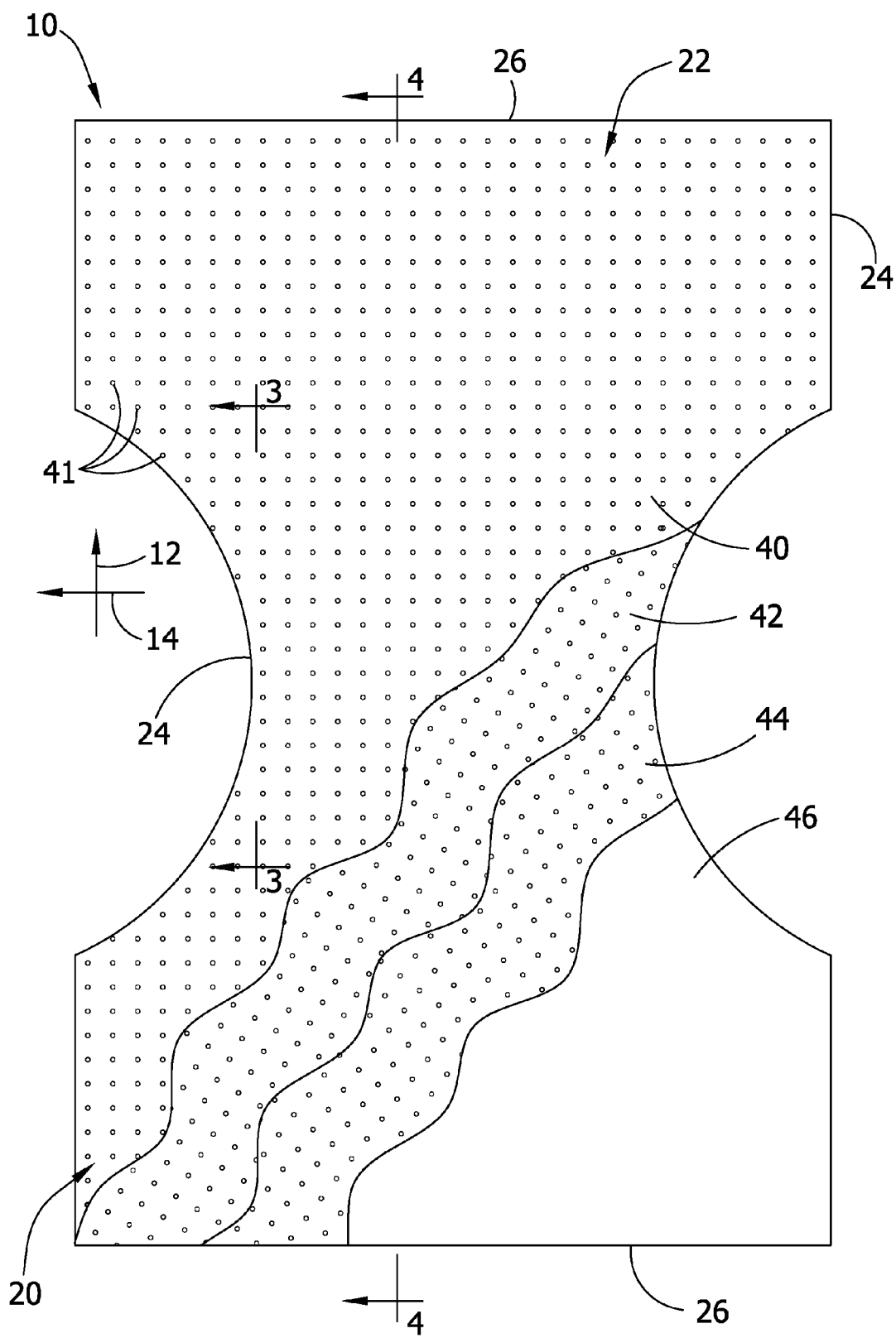
FIG. 1 is a top plan view of a representative absorbent article, broken away to show a microlayered film system embodying the invention.

Referring now to the drawings, and in particular to FIG. 1, for disclosure purposes an absorbent article constructed according to the present invention is shown in the form of a diaper 10 unfolded and laid flat with substantially all elastic induced gathering and contraction features removed. The diaper 10 extends lengthwise in a longitudinal or machine-direction 12 (MD), widthwise in a lateral or cross-direction 14 (CD), and has a depth or thickness direction 16 (TD) (see FIG. 3). For purposes of the present disclosure, the machine-direction 12 lies parallel to the plane of the diaper 10, and extends generally between opposite longitudinal ends of the diaper. The cross-direction 14 also lies parallel to the plane of the article, and is generally transversely oriented or perpendicular relative to the longitudinal MD direction 12. The thickness direction 16 is oriented substantially perpendicular or normal to the plane of both the MD direction 12 and the transverse CD direction 14, and extends through the thickness of the diaper 10. In FIG. 1, the bodyside surface of the diaper which contacts the wearer faces upwardly and the outer edges of the diaper define a periphery with longitudinally extending side edge margins 24 and laterally extending end edge margins 26. The side edges 24 will define leg openings for the diaper 10, in use.

Typical of most absorbent articles to which the invention pertains, the inward or bodyside surface is configured to fit against the body of the wearer when in use, and the outward surface is configured to face away from the wearer's body in use. The absorbent article 10 may have any desired shape, such as rectangular, I-shaped, a generally hourglass shape, or a T-shape.

It will be understood that different absorbent articles to which the invention applies may require different features or combinations and arrangements of parts. The absorbent article selected for disclosure is a child's diaper 10, and a brief discussion of certain diaper features is believed to be relevant including diaper fastening systems and elastomeric gathering members, as now described with reference to FIG. 2.

A diaper fastening system includes a first fastener component in the form of fastener tabs 30 on the back ears of the back waistband portion 20 and a second fastener component in the form of landing zone patches 32 are provided on the front ears of the front waistband portion 22 to hold the diaper 10 snugly in place on a wearer so that the back portion overlaps the front portion. The landing zone patches 32 provide a target area for releasable and re-attachable securement with the fastener tabs 30. It is understood that alternate fastening arrangements (not shown) could be used in which a front waistband portion overlaps the back waistband portion, or alternative fastener tabs and landing patch members can be selectively placed on the first or second waistband portions. The landing zone patches 32 and the fastener tabs 30 can be made of a substantially non-elastomeric material, such as polymer films or tapes that are desirably of a disposable material which may be biodegradable. The landing zone patch 32 could also be made of a substantially elastomeric material, such as a stretch-bonded-laminate (SBL) material, an elastomeric neck-bonded-laminate (NBL) material, an elastomeric film, an elastomeric foam material, or the like which is elastomerically stretchable. In a broad context the aforesaid fastening mechanism between the selected first and second fastener components may be adhesive, cohesive, mechanical or combinations thereof. The mechanical fastening system may be of the hook-and-loop type. Such fastening systems typically include a first attachment member in the form of a "hook" or hook-like, male component used as the tabs 30, and a second member in the form of a cooperating "loop" or loop-like, female component used as the patch 32 and which is engaged and releasably interconnected with the first hook component. Such conventional systems are, for example, available under the VELCRO™.

The diaper typically also has a system of elastomeric gathering members, including leg elastics or cuffs 34 to hold the diaper 10 closely around the legs and a waist elastic 36 (located in the back waistband portion 20) to draw the diaper around the waist. In addition, other elasticized containment flaps 38 may be provided to extend generally lengthwise in the machine-direction 12 of the diaper 10. The containment flaps 38 are typically positioned laterally inboard from the leg elastics 34, and substantially symmetrically placed on each side of the longitudinal centerline of the diaper to closely contact and conform to the contours of the wearer's body. Examples of suitable containment flap constructions are described in U.S. Pat. No. 4,704,116 entitled DIAPERS WITH ELASTICIZED SIDE POCKETS issued Nov. 3, 1987, and U.S. Pat. No. 5,562,650 entitled ABSORBENT ARTICLE HAVING AN IMPROVED SURGE MANAGEMENT issued Feb. 13, 1996, the disclosures of which are incorporated herein by reference as though fully set out. Such containment waist flaps may be composed of a wettable or non-wettable material, as desired, and may be substantially liquid-impermeable, permeable to only gas, or permeable to both gas and liquid.

A typical absorbent article is made up of several components to carry out the requisite functionality of the article. A typical diaper (10) has an intake liner with a body side surface, an interior liquid absorbing core that may be scrim reinforced to provide more strength and integrity, and a backside or barrier liner with an outwardly facing surface. There are many combinations of materials and manufacturing techniques for such conventional prior absorbent article structures. For instance, current personal care absorbent articles typically provide basic leakage protection based on discharge of various human waste at an intake rate (ability to take in urine) at a rate of 2 to 3 g/sec on initial insult of urine and 3 to 5 g/sec on second insult, and with a liquid (urine) holding capacity of 350 to 450 g, preferably, 300 to 500 g. Thus, current personal care absorbent articles provide the above functionality with a plurality of basic components represented by a multitude of regions delivered through various technologies summarized as:

(1) body side liner (intake region), typically nonwoven/fibrous in nature designed to intake liquid at the least of the above described rate, and provide some protection from the flow-back of that liquid to maintain dry skin;

(2) liquid acquisition (surge) or distribution region, typically nonwoven or cellulose/pulp fiber designed to uptake volumes of liquid upon insult, dewater the body side intake liner and deliver the liquid to the main liquid retention center;

(3) retention region typically consists of a blend of cellulose fibers and super absorbent particulates designed to dewater the acquisition region, and store and immobilize the liquid preventing it from flowing back to the skin; and (4) barrier region, typically a liquid impervious film based material designed to provide an absolute barrier to waste, and also may provide breathability to enhance skin dryness. This film region may also contain a fibrous (nonwoven) outer layer to provide cloth-like aesthetics to the outside of the product.

Figure 3:
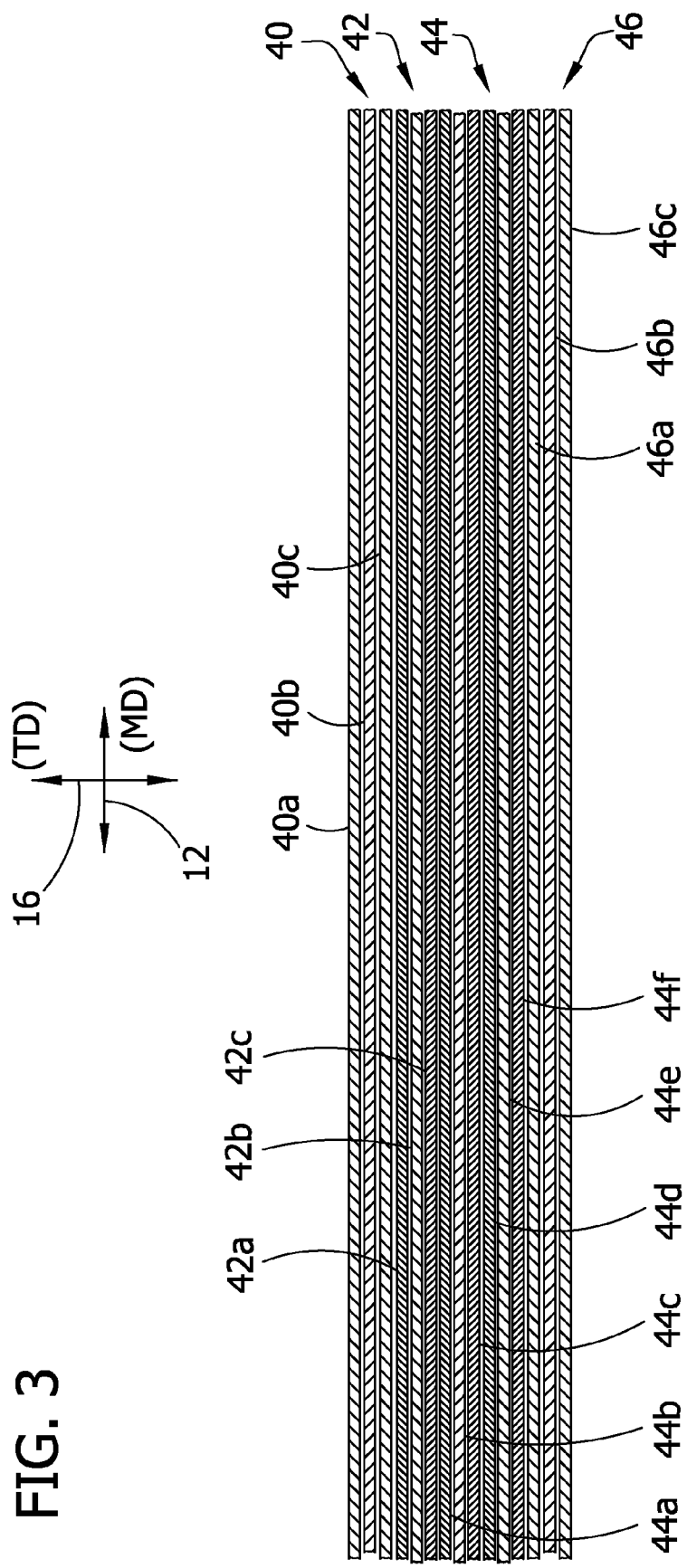
FIG. 3 is an enlarged, fragmentary and schematic sectional view of the absorbent article taken along line 3-3 of FIG. 1, and showing a section of the microlayered film after one stage of manufacture.
Figure 4:
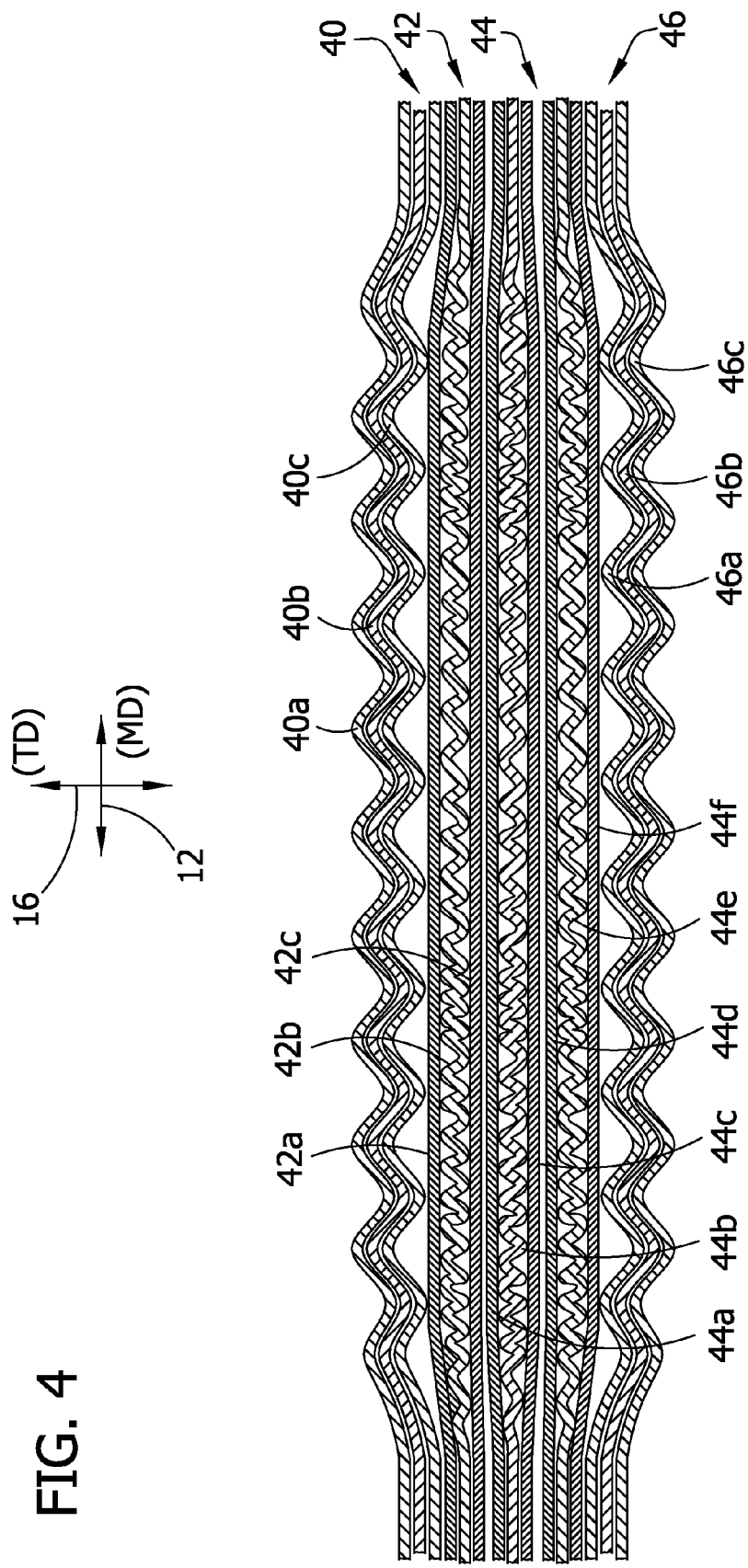
FIG. 4 is an enlarged, schematic sectional view of the absorbent article taken on line 4-4 of FIG. 1 and showing the microlayered film after another stage of manufacture.

The present invention provides all the aforesaid functionality/function components with a single technology (corrugated microlayer film technology). Thus, in the present invention a series of different polymer films are employed to form a unitary absorbent article (e.g., diaper 10) possessing the requisite characteristics to meet the functional requirements thereof. With reference to FIGS. 1, 3 and 4, the present diaper 10 has multiple microlayered film components that are coextruded and treated to form a unified polymer system. These film components may sequentially include an upper, body-facing intake liner function region 40 for the passage of liquid exudates therethrough; an acquisition region, which is an instantaneous uptake (surge) and liquid distribution function region 42 for surge management to rapidly accept, decelerate and diffuse surges or gushes of body liquids and to release and wick such liquids into the main interior absorbent structure; a retention function region 44 of microlayered film for receiving and holding the main volume of liquid exudates; and an outwardly facing barrier function region 46 for retaining the liquids within the retention function region 44 and presenting a dry outer cover surface. As schematically illustrated in FIG. 3, each region is made up of films made up of multiple, coextruded microlayers.

A feature of the present invention is directed to films with corrugated microlayers made by coextrusion of alternating microlayers of thermoplastic, melt extrudable elastomer and melt extrudable, extensible thermoplastic polymer. The films of the present invention may be activated to have corrugated microlayers formed by the melt extrudable elastomer layers, the melt extrudable, extensible thermoplastic polymer layers, or both. At least one of the corrugated microlayers will generally include layers composed of a thermoplastic melt extrudable non-elastomeric polymer. Suitable thermoplastic polymers are stretchable in a solid state and, if required, at elevated temperature which will allow a drawing and thinning of layers during film stretching.

This invention includes multi-microlayer films composed of an assembly of coextruded microlayers of thermoplastic elastomers and polymers. "Multi-microlayer" means a film having a plurality of alternating microlayers wherein, based upon the process by which the film is made, each microlayer becomes partially integrated or adhered with the microlayers above and below the microlayer. Additionally, during formation of the films, which may include stretching, the microlayers will partially delaminate from one another, thereby permitting the corrugations to be formed upon relaxation or activation of the film. However, partial integration or adherence of microlayers remains, unlike certain prior multi-layer films.

The system of this invention includes a plurality of corrugated microlayered films, which may be corrugated in a machine direction and/or a cross-direction to form microchannel spaces and voids. Some or all of the microlayers may be biodegradable. The microlayered films may contain particulate filler material, which upon stretching of the film may provide porosity initiating sites. The film may also include a third microlayer of a melt processable polymer, which may include filler particles and provide for controlled delamination and corrugation of microlayers. The third layer can contain higher levels of fillers or antislip agents to provide controlled delamination, as is known in the art.

The multi-microlayer polymer film of this invention comprises a plurality of coextruded microlayers that form a laminate structure. The coextruded microlayers include a plurality of elastomeric microlayers comprising a first polymer comprising an elastomeric, melt-extrudable polymer and a second polymer comprising an extensible (nonelastic), melt-extrudable polymer capable of forming corrugated microlayers. The plural elastomeric microlayers and other polymer microlayers, including the melt-extrudable, extensible microlayers capable of forming corrugated microlayers, are arranged in a series of parallel repeating laminate units. Each laminate unit comprises at least one of the extensible microlayers and at least one of the elastomeric microlayers. Desirably, each laminate unit has one extensible microlayer laminated to an elastomeric microlayer so that the coextruded microlayers alternate between extensible and elastomeric polymer. Then, after stretching and releasing of the film, corrugations form in the extensible microlayer, the elastomeric microlayer, or both. These corrugations produce microchannels 52 having void spaces 50 between the corrugated and elastomeric microlayers (See FIGS. 3B and 5). Activation using heat or microwave energy might be alternatively used to form corrugations in the stretched film.

Each laminate unit may also include a third microlayer (not shown), as a tie or transition microlayer between the corrugated microlayer and the elastomeric microlayer. The tie microlayer is useful for modifying or enhancing properties of the microlayer film such as softness, opacity, liquid absorption and retention. This tie microlayer may also control debonding/delaminating between the elastomeric and corrugated microlayers thus controlling the frequency and the amplitude of corrugations. The tie microlayer may be formed from a filled thermoplastic polymer and may be formed from thermoplastic water soluble or swellable polymers or superabsorbent materials. For example, the tie microlayer may be formed from thermoplastic, melt extrudable polyethylene oxide resin or melt extrudable polyvinyl alcohol resin. The particular composition of the tie microlayer depends on the elastic and extensible polymers used to form the laminate units.

Corrugations within the film can be formed using the following process. Film formed from multiple laminate units (which may be coextruded) is plastically drawn and thinned by applying a stretching force. When the stretching force is released, the elastomeric microlayers return substantially to their original (unstretched) size. However, the extensible (non-elastic) polymer microlayers do not. As a result, the extensible microlayers are partially debonded from the elastomeric microlayers. The portions of the extensible microlayers which are debonded fold up, forming corrugations under the contraction force provided by the elastomer microlayers returning to their original size. Importantly, other portions of the extensible microlayers remain securely bonded to the elastomeric microlayers. The buckling phenomenon and a formation of corrugations and folds in the drawn thermoplastic microlayers, is a fundamental mechanism for the formation of the film with corrugated microlayers. However, it is also possible to construct the laminate units so that substantially no debonding of the extensible and elastic microlayers occurs, as will be described more fully hereinafter. In that event, the film is corrugated, but the microlayers remain coherent. Drawability and a sufficient stiffness to allow buckling and the formation of corrugations is a characteristic for the extensible microlayer. The polymer that forms the extensible microlayers may be wettable to increase the wicking property of the film.

Figure 5:
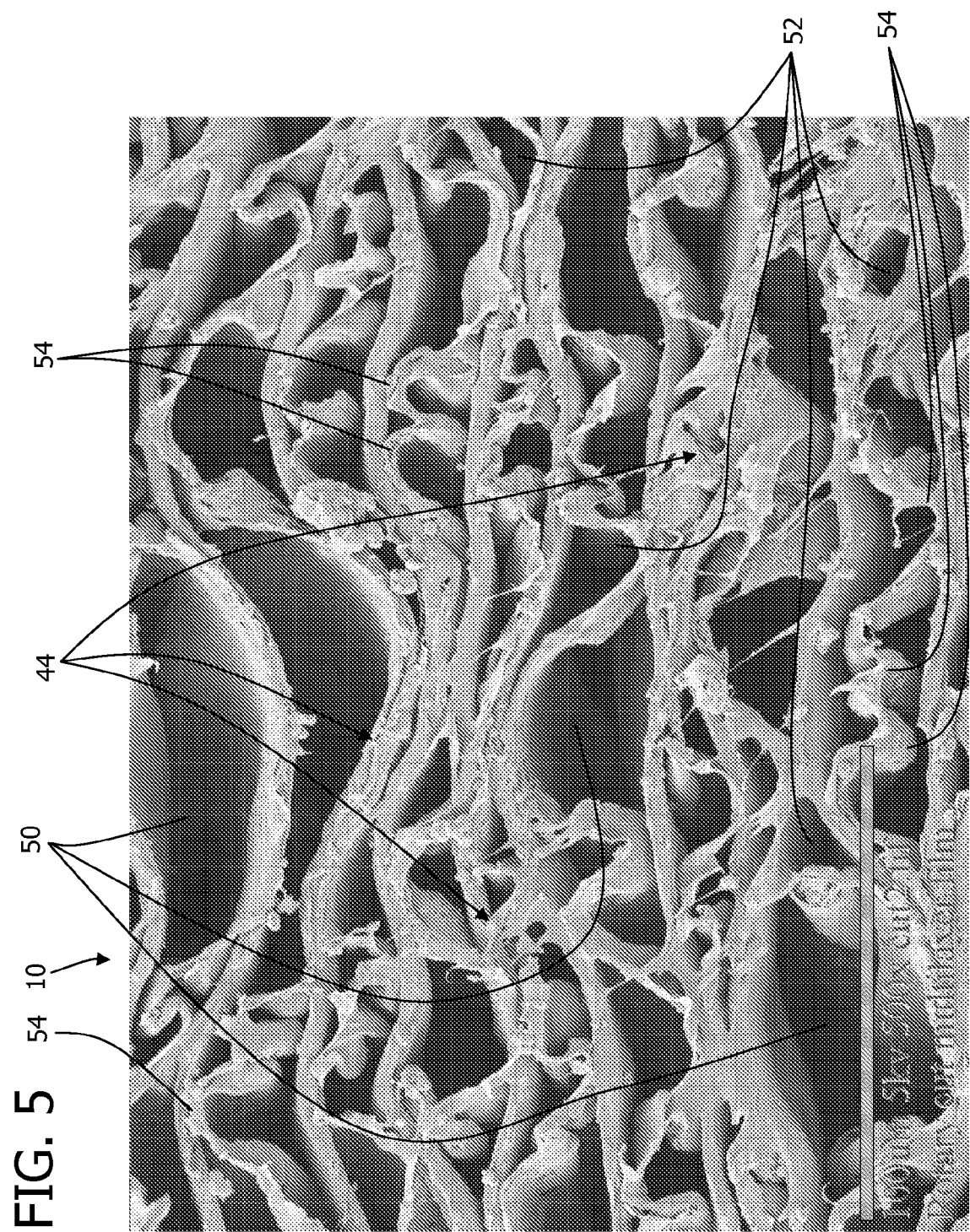
FIG. 5 is a scanning electron microscopy (SEM) micrograph, taken at a magnification of 500×, showing a representative cross-sectional view in the machine direction of a corrugated microlayer film system of the invention.

As seen in FIGS. 4 and 5, during the formation of corrugated microlayers the multilayer film changes dimensions in the direction of stretching and in the TD direction 16. Typically it shrinks in the stretch direction (MD or CD) and expands in thickness providing three-dimensional profiles and structures. Additionally, during this formation, the elastomeric microlayers may also form corrugations (not shown). Any microchannels formed in the elastomeric microlayers will be in a direction substantially perpendicular to the microchannels formed in the melt-extrudable, extensible polymer capable of forming corrugated microlayers.

Microlayered laminate films have high integrity and strength because they do not substantially delaminate after microlayer coextrusion due to the partial integration or strong adhesion. However, the corrugated microlayers will be partially delaminated from the elastomeric microlayers upon formation of the corrugated microlayers. Microlayers enable combinations of two or more microlayers of normally incompatible polymers to form a monolithic film with a strong coupling between individual microlayers without using compatibilizing agents.

Suitable melt-extrudable thermoplastic polymers used in this invention are stretchable in solid state to allow a stretch processing of the multi-microlayered film. Stretching in solid state means stretching at a temperature below the melting point of the thermoplastic polymer. The ratio of true tensile fracture stress (tensile force at failure divided by the cross-sectional area of the failed specimen), and the stress at yielding, is useful to determine the stretchability of the polymer film. In one embodiment, such ratio for suitable melt-extrudable polymers used in this invention ranges from about 1 to about 150, more particularly from about 5 to about 100, and even more particularly from about 10 to about 50.

The thermoplastic elastomer microlayers of the film of this invention are desirably composed of a thermoplastic, melt extrudable polymer. "Elastomeric" means that the polymer may be stretched to several hundred percent of elongation and may recover to about its original dimensions when the stretching force is removed. The function of elastomeric microlayers is to provide a confinement and a sufficient contraction force to corrugating microlayers after the multi-microlayer film is stretched to a specified draw ratio and a stretching force is released. A "precursor multi-microlayer film" is a film that has been formed, but not yet stretched. A precursor multi-microlayer film may have alternating microlayers of the melt extrudable elastomer polymer and the melt extrudable stretchable thermoplastic polymer.

Suitable elastomeric materials that may be used for the elastomeric component of the multi-microlayer film include a melt extrudable thermoplastic elastomer such as a polyurethane elastomer, a copolyether ester, a polyether block polyamide copolymer, an ethylene vinyl acetate (EVA) elastomer, a styrenic block copolymer, an olefinic elastomer, as well as other elastomers known to those skilled in the polymer art. Useful elastomeric resins include polyester polyurethane and polyether polyurethane. Examples of two commercially available elastomeric resins are sold under the trade designations PN 3429-219 and PS 370-200 MORTHANE® polyurethanes. MORTHANE is a trademark of Huntsman Polyurethanes with an office in Chicago, Ill. Another suitable elastomeric material is ESTANE® polyurethane, a trademark of Noveon, Inc. with an office in Cleveland, Ohio. Still another suitable elastomeric material is PEARLTHANE® polyurethane, a trademark of Merquinsa with an office in Boxford, Mass.

Three additional elastomeric materials include a polyether block polyamide copolymer which is commercially available in various grades under the trade designation PEBAX®. PEBAX® is a trademark of Atofina Chemicals, Inc. with an office in Birdsboro, Pa. A second elastomeric material is a copolyether-ester sold under the trade designation ARNITEL®. ARNITEL is a trademark of DSM with an office at Het Overloon 1, NL-6411 TE Heerlen, Netherlands. The third elastomeric material is a copolyether-ester sold under the trade designation HYTREL®. HYTREL is a trademark of E.I. DuPont de Nemours with an office in Wilmington, Del. The elastomeric component may also be formed from a styrenic block copolymer such as KRATON®. KRATON is a trademark of Kraton Polymers having an office in Houston, Tex.

The elastomeric component may further be formed from a biodegradable elastomeric material such as polyester aliphatic polyurethanes or polyhydroxyalkanoates. The elastomeric component may also be formed from an olefinic elastomeric resin, such as elastomers and plastomers including single-site catalyzed or metallocene catalyzed polyethylene, polypropylene and other alpha-olefin homopolymers and copolymers, having density less than about 0.89 grams/cc. One such plastomer is an ethylene-based resins and/or polymers sold under the trade designation AFFINITY®. AFFINITY® is a registered trademark of Dow Chemical Company having an office in Freeport, Tex. Another plastomer is sold under the trade designation EXACT® which is a trademark of Exxon Mobil Corporation with an office in Irving, Tex. The corrugated microlayers of the film of this invention may include a thermoplastic non-elastomer polymer component that may be biodegradable or non biodegradable, or combinations, blends or mixtures thereof. The thermoplastic non-elastomer polymer should be melt-extrudable so that the polymer may be coextruded along with the elastomeric polymer to form the microlayer film. In addition, the elastomer polymer component and/or the thermoplastic non-elastomer polymer component may be permeable to water vapor when in the form of a film. Finally, the thermoplastic non-elastomer polymer component polymer is selected such that the polymer is capable of being formed into a corrugated microlayer. By "capable of being formed into a corrugated microlayer" it is meant that after the thermoplastic non-elastomer polymer and elastomeric polymer are coextruded, stretching of the coextruded film will cause the thermoplastic non-elastomer polymer to partially debond from the elastomeric microlayer such that when the stretching force is removed, the elastomeric polymer recovers more of its original shape than the thermoplastic non-elastomer polymer component microlayer, thereby causing partial delamination and corrugations to form in the thermoplastic non-elastomer polymer component microlayers.

Suitable biologically degradable polymers are characterized by being degraded in the presence of naturally occurring microorganisms. Evidence of such degradation is that the films break down into smaller pieces or lose strength significantly when the films are placed in a biologically-active environment, (i.e. composting or sludge digestion). Biodegradability is also demonstrated by a polymeric material that, when composted under standard conditions for 45 days, at least 60% of the organic carbon is converted to carbon dioxide, relative to a positive reference material (cellulose=100%). The American Society for Testing and Materials (ASTM) Standard Test Method for Determining Aerobic Biodegradation of Plastic Materials Under Controlled Composting Conditions, designation D 5338-98, is used for this determination. Biologically degradable polymers useful in the present invention include, but are not limited to, biodegradable aliphatic polyesters, polymers and copolymers of polycaprolactone, polymers and copolymers of polylactic acid (PLA), polyhydroxy alkanoates of various composition and molecular weights and their copolymers, polymers and copolymers of polybutylene succinate, poly(butylene succinate-adipate), other biodegradable melt extrudable polymers and copolymers, and blends and mixtures thereof.

Biodegradable resins useful for this invention also include aliphatic-aromatic co-polyesters sold under the trade designation EastarBio™, a trademark of Eastman Chemical Company with an office in Kingsport, Tenn. Another aliphatic-aromatic co-polyester is sold under the trade designation Ecoflex®, a trademark of BASF Corporation with an office in Mount Olive, N.J. Still another useful biodegradable resin is thermoplastic polyesteramide available from Baer Corporation having an office in Pittsburgh, Pa. Polylactic acid polymers and copolymers useful in this invention are melt-stable, semi-crystalline resins disclosed in U.S. Pat. No. 5,773,562 entitled Melt-Stable Semi-Crystalline Lactide Polymer Film and Process for Manufacture Thereof. Examples of commercially available PLA resins include Lacty® from Shimadzu Corporation, Lacea® from Mitsui Chemicals, NatureWorks™ PLA from Cargil Dow LLC with office in Minnetonka, Minn.

The biodegradable polymer or non-biodegradable polymer may include plasticizers, surfactants, solid-state modifiers, processing aids, and other additives to improve melt processability, reduce viscosity, enhance drawability/stretchability in a solid state, and improve surface properties and thermal stability. Surfactants and additives may also improve wettability and interactions with liquids. In addition, grafting, copolymerization, and modification of end groups may be used to modify the surface properties of the corrugating microlayered films. A non-biodegradable, melt extrudable and stretchable component for corrugating microlayer may be formed from polyolefins, a polyester, a polyether, its copolymers, or blends and mixtures thereof. Examples of non-biodegradable, melt extrudable and stretchable polymers may include polypropylene and its copolymers, polyethylene and its copolymers, and blends and mixtures thereof. Non-biodegradable polymers may include plasticizers, surfactants and other additives which may modify and improve the performance and processability of the film. A specific example includes polypropylene resin H 702-35NA obtained from Dow Chemical Company with an office in Midland, Mich. Polypropylene and its copolymers are useful in the present invention as a non-biodegradable polymer due to its stiffness, good processability, ability to accept fillers and stretchability.

A principal object of the present invention is to form the intake region 40, distribution region 42, retention region 44 and barrier region from microlayer film of the type just described. The configurations of the microlayers are controlled so that the various functions of these layers may be achieved. The intake function region 40 is designed to rapidly move liquid away from the skin to the distribution region 42 and provide softness and tactile properties for skin dryness and skin health. To provide rapid intake the intake-function region 40 can be perforated throughout (at 41 in FIG. 1) using any known in the art methods such as vacuum aperturing mechanical perforation/aperturing, water-jet perforation, laser beam aperturing, ultrasonic perforation or other techniques. One example of another technique is using materials for the microlayers having filler materials incorporated therein of particle sizes in the range of 5 to 250 microns. Generally speaking, the particles may be on the order of five to ten times larger than the thickness of the microlayer in which they are embedded to produce apertures. Filler impregnated materials of this type will form apertures upon stretching of the material. The microlayer material tends to partially detach from the particle upon stretching, thereby forming apertures. The particles may also have the benefit of enhancing the interconnection of various microlayers in a microlayer film. Because the particles are so much larger than the thickness of one microlayer, they extend through and are attached to several microlayers in the film, increasing the cohesion of the microlayers.

Perforation may be accomplished by punching holes using pins of varying diameter, configuration and number per square inch. As stated above, a typical first insult intake rate is 2-3 g/sec, and 3-5 g/sec for a second insult. The perforations 41 can be of various shape and geometry, preferably having conical shape to prevent liquid flow back. Hole size can vary from about 5 mm to about 0.25 mm; or may vary from about 1.5 mm to about 0.5 mm, and still further may vary from about 1.25 mm to about 0.75 mm. The number of holes per unit surface area in the intake liner can vary from about 2 holes to about 31 holes per sq. cm (10 to 200 holes per sq. inch); from about 8 holes to about 23 holes per sq. cm (50 holes to 150 holes per sq. inch) and from about 12 holes to about 19 holes per sq. cm (75 to 125 holes per sq. inch) in different embodiments. The aggregate area of the holes or "open area" may represent in different embodiments from about 30% to about 90% of the surface area of the microlayer film in that region, from about 45% to about 85% of the surface area, or from about 60% to about 80% of the surface area.

Figure 3A:
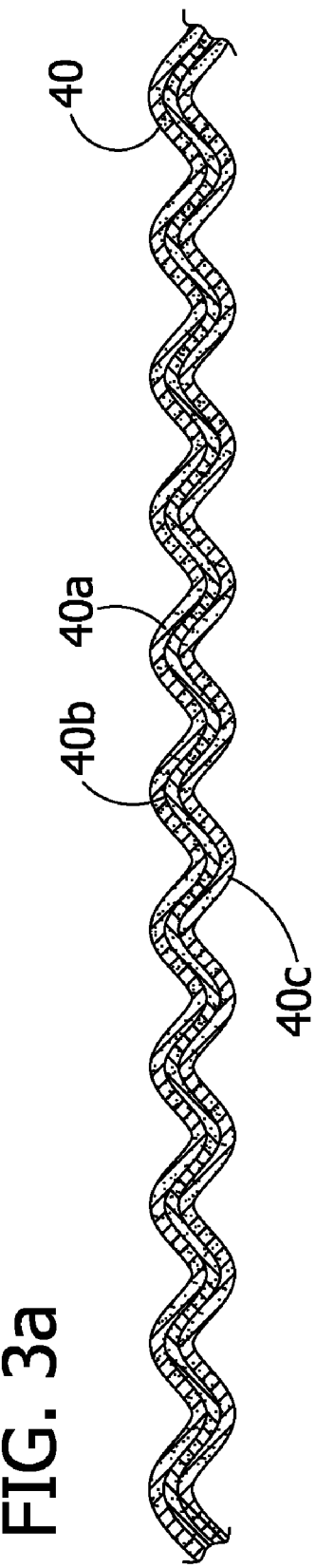
FIG. 3a is an enlarged, fragmentary and schematic sectional view of microlayers in an intake region which have not delaminated upon relaxation of a stretching force applied thereto.

To provide softness and good tactile properties the intake function region 40 desirably has surface corrugations (FIG. 3a). The corrugations may range in amplitude, for example, from about 5 mm to about 0.01 mm for one embodiment, from about 2 mm to about 0.25 mm in another embodiment, and from about 1 mm to about 0.05 mm in a still further embodiment. It will be understood that the corrugations will not be uniform in amplitude. The intake function region 40 may be formed of multiple microlayers (e.g., schematically illustrated as three microlayers 40a, 40b, 40c). The surface corrugations can be formed by stretching coextruded microlayer film 40 having the alternating elastomeric and extensible layers 40a, 40b, 40c and allowing the film to relax (as described previously). For the intake region 40, the microlayers are configured so that, in one embodiment (FIG. 3a), no delamination occurs after the microlayers are stretched and released. In the resulting coherent structure, both the elastomeric layers (e.g., 40a and 40c) and extensible layer (e.g., 40b) are corrugated. One way to create a non-delaminated microlayer structure of this type is to limit the extensible microlayer thickness to about 0.5 microns, with the elastomeric layer being thicker. Generally speaking, the elastomeric microlayer might be about 30% thicker than the extensible microlayer for inhibiting delamination.

Figure 3B:
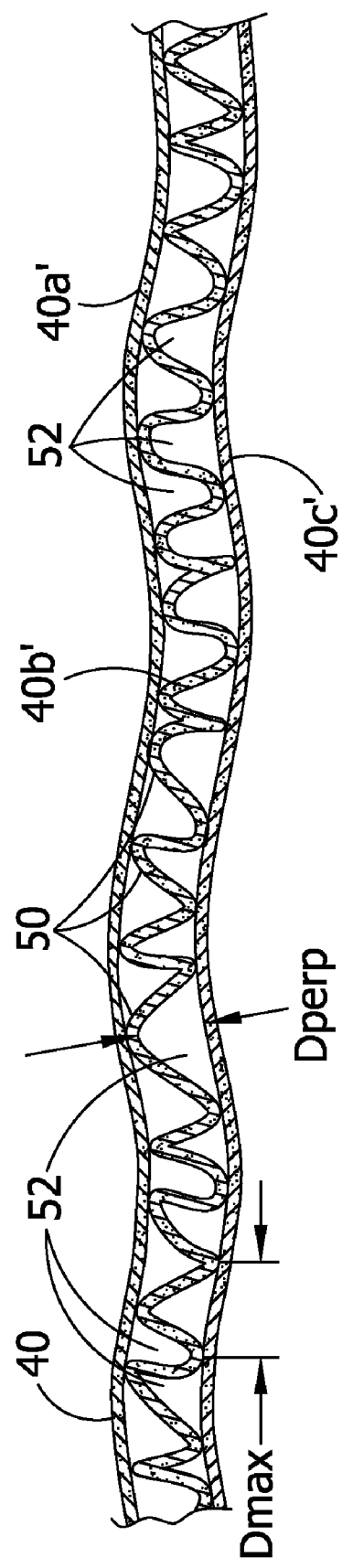
FIG. 3b is an enlarged, fragmentary and schematic sectional view of microlayers in an intake region which partially delaminated and internally corrugated upon relaxation of a stretching force applied thereto.

It will be understood that the intake region 40 may also be formed of plural film microlayers 40a', 40b', 40c' that are coextruded and stretched, but which are configured to partially delaminate upon relief of the stretching force to provide an internally corrugated intake region structure, as schematically illustrated in FIG. 3b. If internal microchannels 50 are formed by delamination of the microlayers, the microchannel size may range from about 10 microns to about 500 microns. It will be understood that the size of the microchannels will not be uniform. In general, it is desirable for these microchannels 52 in the intake region 40 to be large to facilitate the easy movement of liquid through the microchannels. Microlayer corrugation (whether or not the microlayers remain connected or are partially delaminated) can provide for softness, conformability, stretchability and drape of the intake region 40. Although three microlayers 40a, 40b, 40c are shown, many more microlayers may be used to form the entire region.

Figure 2:
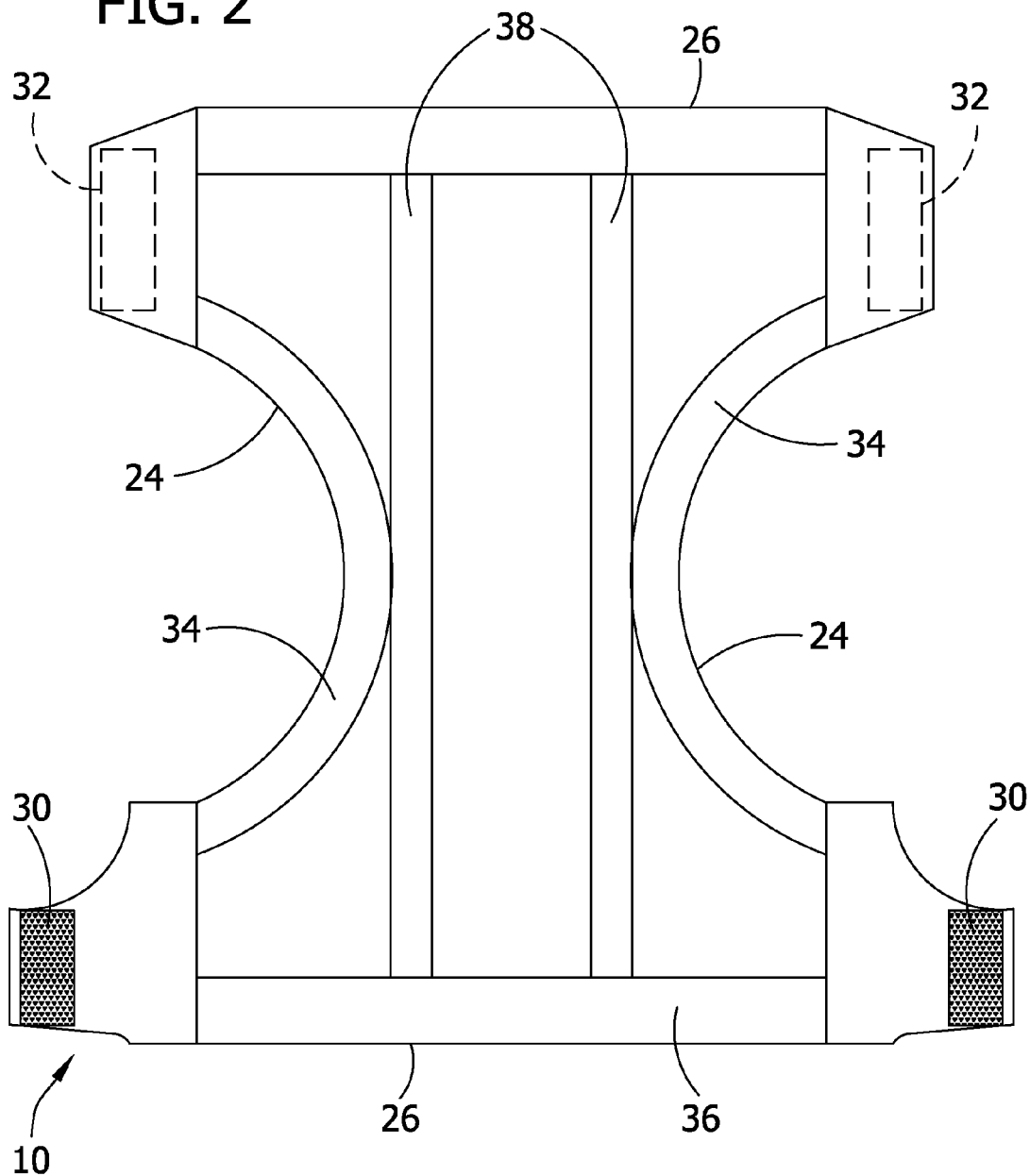
FIG. 2 is a plan view of the absorbent article of FIG. 1 as finished with fitting components for use.

The uptake and distribution function region 42 may be formed of plural film microlayers (schematically illustrated by three microlayers 42a, 42b, 42c in FIGS. 2 and 4), which may also be perforated with aperture sizes and densities similar to intake function region 40. The distribution region 42 should have sufficient void volume and vertical wicking potential to acquire and distribute liquid. The density of distribution region 42 can vary, for example, from about 0.015 g/cc to about 0.05 g/cc in one embodiment and from about 0.02 g/cc to about 0.03 g/cc in another embodiment. Microchannels formed by stretching and partial delamination in the distribution-function region 42 have a size distribution which provides for a vertical wicking of liquid up to 15 cm height, more preferably up to 20 cm height. The microchannels can vary in size in one embodiment, from about 5 microns to about 100 microns, and in another embodiment from about 10 microns to about 150 microns, and still in another embodiment from about 20 microns to about 80 microns. Generally speaking, the size of the microchannels in the distribution region 42 will be smaller than those in the intake region 40 to promote wicking and desorption of the intake layer.

The retention region 44 needs to have a large liquid retention capacity. For example, the retention region may have an absorption capacity varying from about 300 g to about 500 g of saline in one embodiment, and from about 350 g to about 450 g in another embodiment. Stated another way, the retention region 44 might desirably have an absorbent capacity of at least about 10 g of saline per gram of microlayer film in the retention region. To get fluid into the retention region 44 formed of the extruded microlayers (e.g., microlayers 44a-44f), the region may have perforations similar to those of the intake region 40 and the distribution region 42. The retention region 44 is shown with six microlayers (44a-44f) to indicate that there may be desirably more microlayers in this region. However, the exact number and arrangement of the microlayers in each region may be other than shown and described without departing from the scope of the present invention. In addition, the microlayers of the retention region 44 may incorporate microholes formed by incorporating a filler material (e.g., $CaCO_3$) into the microlayer material that causes such holes to form upon stretching. The formation of such microholes is described in more detail hereinafter with regard to making the barrier region 46 breathable.

In order to obtain the necessary fluid retention, superabsorbent material (SAM) may be incorporated into the retention region 44. There are several ways in which this might be accomplished. A layer or coating of SAM can be bonded or otherwise attached directly to the microlayers forming the retention region 44. For instance, microlayers of an elastic and extensible material might be coextruded with microlayers of SAM. It is also possible to blend small particle size superabsorbent with one or both of the components of the microlayers prior to coextrusion. Still further, SAM can be placed in solution and applied to the coextruded microlayer film of the retention region 44. The region is allowed to dry which causes SAM to be deposited on the walls of the internally formed microchannels. A thermoplastic superabsorbent layer formed from a swellable polyurethane could also be used.

The microchannels are of a suitable size for a given function of a particular region of the diaper 10. In any region, the geometry of the microchannels is irregular. In the context of the present invention, the "size" of a collection of microchannels is determined in the following manner. A photomicrograph, electron micrograph, or similar imaging technique is taken of a cross-section of the collection of microchannels of interest. Microchannels 52 in FIGS. 3b and 5 are exemplary, keeping in mind that FIG. 3b is a schematic representation. A set of at least five clearly defined microchannels 52, which appear in the micrograph to be cut by the cross section perpendicularly to the longitudinal axis of the microchannel, are selected from the micrograph. The largest cross-sectional dimension of each microchannel is measured and recorded as $D_{max1}$, $D_{max2}$, $D_{max3}$, $D_{max4}$, $D_{max5}$, etc. The cross-sectional dimension of each microchannel 52 is then measured at right angles to the preceding measurements ($D_{max1}$, etc.), and recorded as $D_{perp1}$, $D_{perp2}$, $D_{perp3}$, $D_{perp4}$, $D_{perp5}$, etc. The geometric mean dimension is calculated for each microchannel 52, i.e., $\{D_{max1} \times D_{perp1}\}^{1/2}$, $\{D_{max2} \times D_{perp2}\}_{1/2}$, etc. The measurements $D_{max}$ and $D_{perp}$ are schematically illustrated in FIG. 3b. The measurements are illustrated at two different microchannels 52 only for clarity of illustration. Both measurements are made for each selected microchannel, as described herein. The arithmetic mean of the geometric mean dimensions for all five (or more) selected and measured microchannels 52 is then calculated to yield the "size" of the microchannels in the particular region of the diaper 10.

In one embodiment, the microchannels 52 may have a size in a range of about 10 microns to about 2000 microns. In another embodiment, the size of the microchannels may range from about 50 microns to about 500 microns. Generally, it is desirable that the retention region 44 has microchannels of a smaller size than the microchannels of the intake region 40 and distribution region 42. In one embodiment, the size of the microchannels in the retention region 44 is less than either the size of the intake region microchannels or less than the size of the distribution region microchannels. In a further embodiment, the size of the retention region microchannels is less than half of the size of the smaller of the intake region microchannels and distribution region microchannels.

The barrier function region 46 may desirably be breathable. Breathable as used herein indicates a significant permeability to water vapor, as well as other gases such as $CO_2$ and $O_2$. The breathability of the multi-microlayer film with corrugated microlayers is expressed as water vapor transmission rate (WVTR, measured in units of g/day/m² of water vapor passing through the material). The WVTR is a function of film thickness, multi-microlayer composition, amount of stretch and microlayer corrugations. In one embodiment, the corrugated film may deliver breathability of up to about 2,500 WVTR; desirably about 5,000 WVTR and more desirably about 25,000 WVTR. It will be understood that while vapor transmission is desirable, the transmission of liquid, or retention of liquid in the barrier layer is not. Accordingly, the microlayers (46a, 46b, 46c) forming the barrier region 46 do not require perforations or internal microchannels. However, the barrier region 46 may have surface corrugations to improve softness, drapability and elastic stretching. The amplitude of such corrugations might be in the range of about 50 microns to about 2 mm. If the barrier region 46 is formed with internal microchannels (as a result of partial delamination), they might have a size in the range of about 5 microns to about 200 microns, or also in a range of about 10 microns to about 100 microns (for example).

A suitable technique for determining the WVTR value of a film is the test procedure standardized by INDA (Association of the Nonwoven Fabric Industry), number IST-70.4-99, which is incorporated by reference herein. The testing device which may be used for WVTR measurement is known as the Permatran-W Model 100K manufactured by Mocon/Modern Controls, Inc., with an office in Minneapolis, Minn. Barrier function region 46 comprises sufficient amount of filler particles to provide for a desired level of breathability. Filler loading in individual microlayers can vary from about 30% to about 60% by weight in one embodiment, and may vary from about 40% to about 55% by weight in another embodiment. Particulate filler material creates discontinuity in the microlayers to provide pathways for water vapor to move through the film. Particulate filler material may also enhance the ability of the microlayer film to absorb or immobilize liquid, enhance biodegradation of the film, provide porosity-initiating debonding sites to enhance the formation of pores when the microlayer film is stretched, improve processability of the microlayer film and reduce production cost of the microlayer film. Surface active materials such as surfactants coated on the filler material may reduce the surface energy of the film, increase hydrophilicity of the film, reduce film stickiness, provide lubrication, or reduce the coefficient of friction of the film.

Suitable filler materials may be organic or inorganic, and are desirably in a form of individual, discreet particles. Suitable inorganic filler materials include metal oxides, hydroxides, carbonates, and sulfates, and various kinds of clay, silica, alumina, powdered metals, glass microspheres, or vugular void-containing particles. Particularly, suitable filler materials include calcium carbonate, barium sulfate, sodium carbonate, magnesium carbonate, magnesium sulfate, barium carbonate, kaolin, carbon, calcium oxide, magnesium oxide, aluminum hydroxide, and titanium dioxide. These filler materials may improve toughness, softness, opacity, vapor transport rate (breathability), biodegradability, liquid immobilization and absorption, skin wellness, odor absorption and other beneficial attributes of the microlayer film. Suitable commercially available filler materials include the following:

1. SUPERMITE®, an ultrafine ground $CaCO_3$, which is available from Imerys of Atlanta, Ga. This material has a top cut particle size of about 8 microns and a mean particle size of about 1 micron.

2. SUPERCOAT®, a coated ultrafine ground $CaCO_3$, which is available from Imerys of Atlanta, Ga. This material has a top cut particle size of about 8 microns and a mean particle size of about 1 micron.

3. OMYACARB® UF, high purity, ultrafine, wet ground $CaCO_3$, which is available from OMYA, Inc., of Proctor, Vt. This material has a top cut particle size of about 4 microns and an average particle size of about 0.7 microns and provides good processability.

4. OMYACARB® UFT $CaCO_3$, an ultrafine pigment surface coated with stearic acid, available from OMYA, Inc. This material has a top cut particle size of about 4 microns and a mean particle size of about 0.7 microns and provides good processability.

The filler may also include superabsorbent particles such as finely ground polyacrylic acid or other superabsorbent materials or other absorbent materials such as carboxy methyl cellulose. The superabsorbent filler in the film with corrugated microlayers may provide absorption of liquids and may expand into the void spaces provided by the corrugating microlayers and improve liquid wetting, liquid retention, liquid absorption and distribution properties.

Surfactants or like surface active materials may increase the hydrophilicity and wettability of the film, and enhance the water vapor permeability of the film, and may improve filler dispersion in the polymer. For example, surfactant or the surface active material may be blended with the polymers forming elastomer microlayers and corrugating microlayers or otherwise incorporated onto the particulate filler material before the filler material is mixed with the elastomeric polymer or the corrugated polymer.

Suitable surfactants and surface-active materials for blending with the polymeric components of the microlayer film, or treating or surface coating the particulate filler material include silicone glycol copolymers, ethylene glycol oligomers, acrylic acid, hydrogen-bonded complexes, carboxylated alcohol, ethoxylates, various ethoxylated alcohols, ethoxylated alkyl phenols, ethoxylated fatty esters, stearic acid, behenic acid, and the like, as well as combinations thereof. Suitable commercially available surfactants include the following:

1. Surfactants composed of ethoxylated alkyl phenols, such as Igepal RC-620, RC-630, CA-620, 630, 720, CO-530, 610, 630, 660, 710, and 730, which are available from Rhone-Poulenc, Inc. of Cranbury, N.J.

2. Surfactants composed of silicone glycol copolymers, such as Dow Corning D190, D193, FF400, and D1315, available from Dow Corning of Midland, Mich.

3. Surfactants composed of ethoxylated mono and diglycerides, such as Mazol® 80 MGK, Masil® SF 19, and Mazol® 165 C, available from PPG Industries of Gurnee, Ill.

4. Surfactants composed of ethoxylated alcohols, such as Genapol 26-L-98N, Genapol 26-L60N, and Genapol 26-L-5 which are available from Hoechst Celanese Corporation of Charlotte, N.C.

5. Surfactants composed of carboxylated alcohol ethoxylates, such as Marlowet 4700 and Marlowet 4703, which are available from Huls America, Inc. of Piscataway, N.J.

6. Ethoxylated fatty esters, such as Pationic 138C, Pationic 122A, Pationic SSL, which are available from R.I.T.A. Corporation of Woodstock, Ill.

The barrier function region 46 comprises corrugated microlayer film especially microlayers at the exterior of the product. Microlayer corrugations (54) can improve tactile and touch properties, improve drape and conformability, reduce noisiness, and provide stretch. The amplitude of surface corrugations can vary from about 2 mm to about 0.01 mm in one embodiment; and from about 1 mm to about 0.025 mm in another, and still further from about 1 mm to about 0.05 mm. The barrier function region is not perforated to thereby provide a liquid barrier of at least about 100 mbar of hydrohead.

Microlayered film can be coextruded with a variety of properties that can differ from the topside intake region 40, inside liquid absorbent and retention regions 42, 44, and backside or barrier region 46. The physical properties of the multi-region film system can be adjusted by tailoring polymer formulation for absorbency/retention, liner properties, stretch properties, barrier properties or post-formulation treatment such as elongation (stretching) and retraction to create corrugations 54 with voids 50 and microchannels 52 within the structure. It will be understood that a microlayer film of the present invention can be formed to include regions which, upon activation as by stretching to form corrugations and microchannels, have different functions. Thus, a single piece of microlayer film has the potential to form two or more of the regions 40, 42, 44, 46. If the activated microlayer film forms less than all of the functional regions 40, 42, 44, 46, it may be assembled together with one or more other activated microlayer films having the functionality of the other regions. Moreover, such a microlayer film may be assembled with other diaper components (not shown) made of conventional, nonmicrolayer material.

Figure 6:
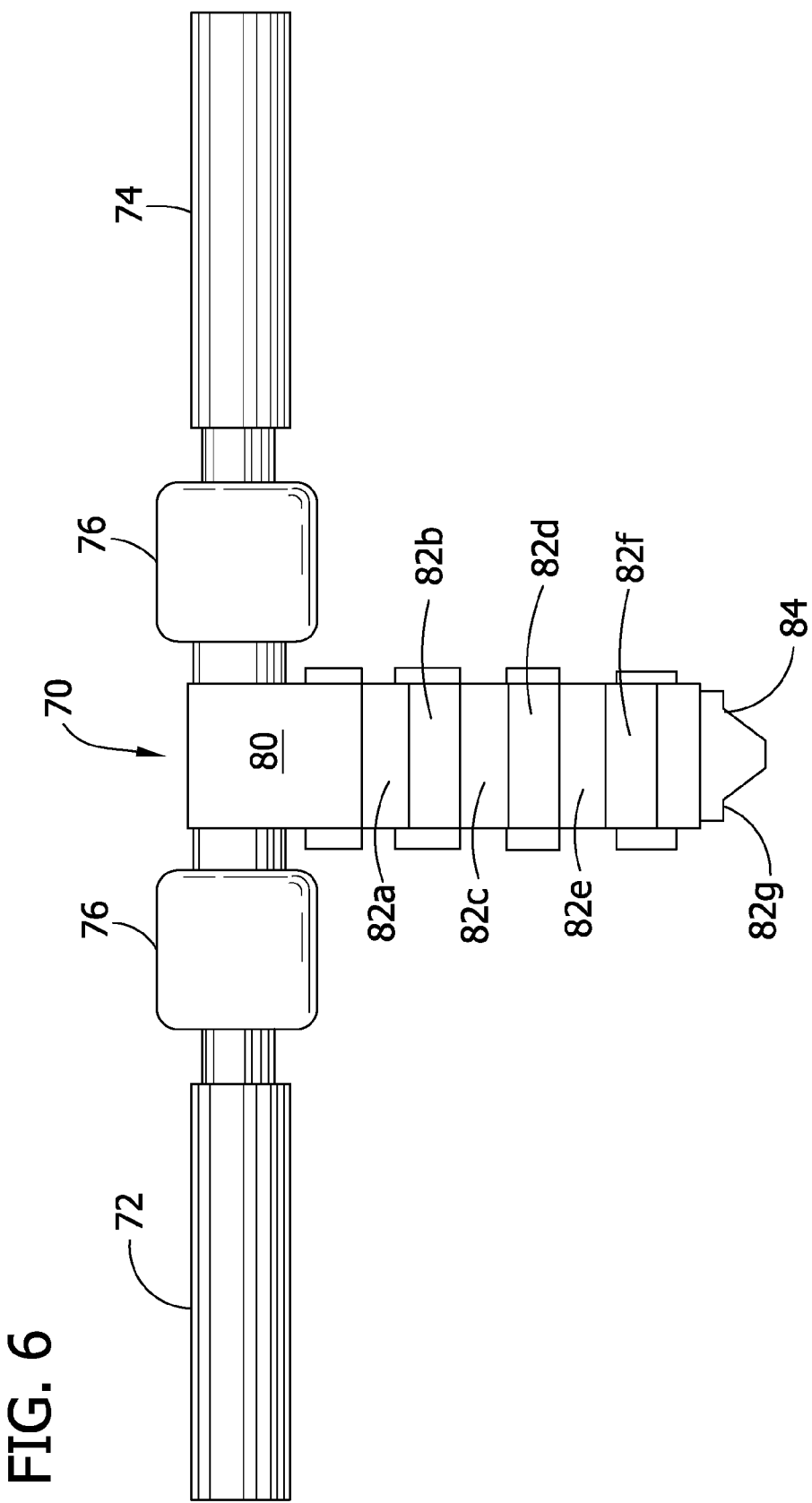
FIG. 6 is a plan view of a coextrusion system useful for making a microlayer polymer film system or subsystem in accordance with embodiments of the invention.

A suitable method for making the microlayer films of this invention is a microlayer coextrusion process wherein two or more polymers (e.g., polypropylene for the extensible microlayer and polyurethane for the elastomeric microlayer) are coextruded to form a laminate unit with two or more microlayers, which laminate unit can then be manipulated to multiply the number of layers in the film. FIG. 6 illustrates a coextrusion device 70 for forming microlayer films. This device includes a pair of opposed single-screw extruders 72 and 74 connected through respective metering pumps 76 and 78 to a coextrusion block 80. A plurality of multiplying elements 82a-g extends in series from the coextrusion block perpendicularly to the single-screw extruders 72 and 74. Each of the multiplying elements includes a die element (not shown) disposed in the melt flow passageway of the coextrusion device. The multiplying elements split the extrusion flows into increasingly finer layers, while retaining the material identity of each layer. The last multiplying element 82g is attached to a discharge nozzle 84 through which the final product extrudes. While single-screw extruders are shown, the present invention may also use twin-screw extruders to form the films of the present invention. The extruded microlayers are sent to a film die (not shown) which spreads the microlayers out into a film. The various microlayers continue to maintain their separate identities within the film. The film may be embossed or perforated.

To make a corrugated microlayer film using the coextrusion device 70 illustrated in FIG. 6, an elastomeric polymer is extruded through the first single screw extruder 72 into the coextrusion block 80. Likewise, a thermoplastic non-elastic polymer, such as polylactic acid or polypropylene, is extruded through the second single screw extruder 74 into the same coextrusion block 80. In the coextrusion block 80, a two-layer melt laminate structure is formed and then extruded through the series of multiplying elements 82a-g to form a multi-layer microlayered laminate with alternating film microlayers of different polymers. The foregoing microlayer coextrusion device and process is described in more detail in an article Mueller et al., entitled Novel Structures By Microlayer Extrusion-Talc-Filled PP, PC/SAN, and HDPE-LL-DPE, Polymer Engineering and Science, Vol. 37, No. 2, 1997. A similar process is described in U.S. Pat. No. 3,576,707 and U.S. Pat. No. 3,051,453. Other processes known in the art to form multi-microlayer film may also be employed, e.g., coextrusion processes described in W. J. Schrenk and T. Ashley, Jr., "*Coextruded Multilayer Polymer Films and Sheets, Polymer Blends*", Vol. 2, Academic Press, New York (1978).

The relative thickness of the microlayers to be corrugated and elastomeric microlayers of the film made by the foregoing process may be controlled by varying the feed ratio of the polymers into the extruders, thus controlling the constituent volume fraction. Controlling the relative thicknesses of the elastomeric and corrugating microlayers can have a substantial impact on the construction and functionality of the resulting laminate unit and film. For instance, the thinner the corrugating microlayer, the more buckling which will occur. The greater the number and smaller the size of microchannels formed by the corrugations, the greater the liquid retention of the region. Thus for example, the uptake and distribution region 42 may have larger microchannels for distributing, and the retention region 44 may have smaller microchannels to retain the liquid. In addition, one or more extruders may be added to the coextrusion device to increase the number of different polymers in the microlayer film. For example, a third extruder may be added to add a SAM tie layer to the film. The same two materials may form the alternate microlayers throughout the thickness of the film. However, different materials could be included in the extrusion, for instance, at the opposite outside surfaces of the film to form a skin. Moreover, particulate SAM could be mixed with polypropylene and then extruded to form high absorbency microlayers. In still another embodiment, grooved roll stretching in the machine direction (MD), cross direction (CD) or both may be applied. Combinations of the techniques described herein may also be used.

The microlayer film may be corrugated by subjecting the film to a selected plurality of stretching operations, such as a uniaxial stretching operation or a biaxial stretching operation. Stretching operations may provide microporous microlayer film with a distinctive porous microlayered morphology, may enhance water vapor transport through the film, and may improve water access, enhance degradability of the film, and enhance elastomeric properties of the film. In a first embodiment, the film is stretched from about 100 to about 1500 percent of its original length. In another embodiment, the film is stretched from about 100 to about 500 percent of its original length. In still a further embodiment, microstretching may be employed, in which localized areas of the material are stretched very short distances, such as a few millimeters.

The parameters during stretching operations include stretching draw ratio, stretching strain rate, and stretching temperature. Stretching temperatures may be in the range of from about 15° C. to about 100° C. In another embodiment, stretching temperatures may be in the range of from about 25° C. to about 85° C., and still further in the range of about 60° C. to about 80° C. During stretching operations, the multi-microlayer film sample may optionally be heated to provide a desired effectiveness of the stretching. Annealing the film after the stretch force is released can soften the (e.g., polypropylene) corrugating microlayers, enhancing the formation of corrugations. In addition, elastomers (e.g., polyurethane) retract more fully to their original size under anneal conditions.

Figure 7:
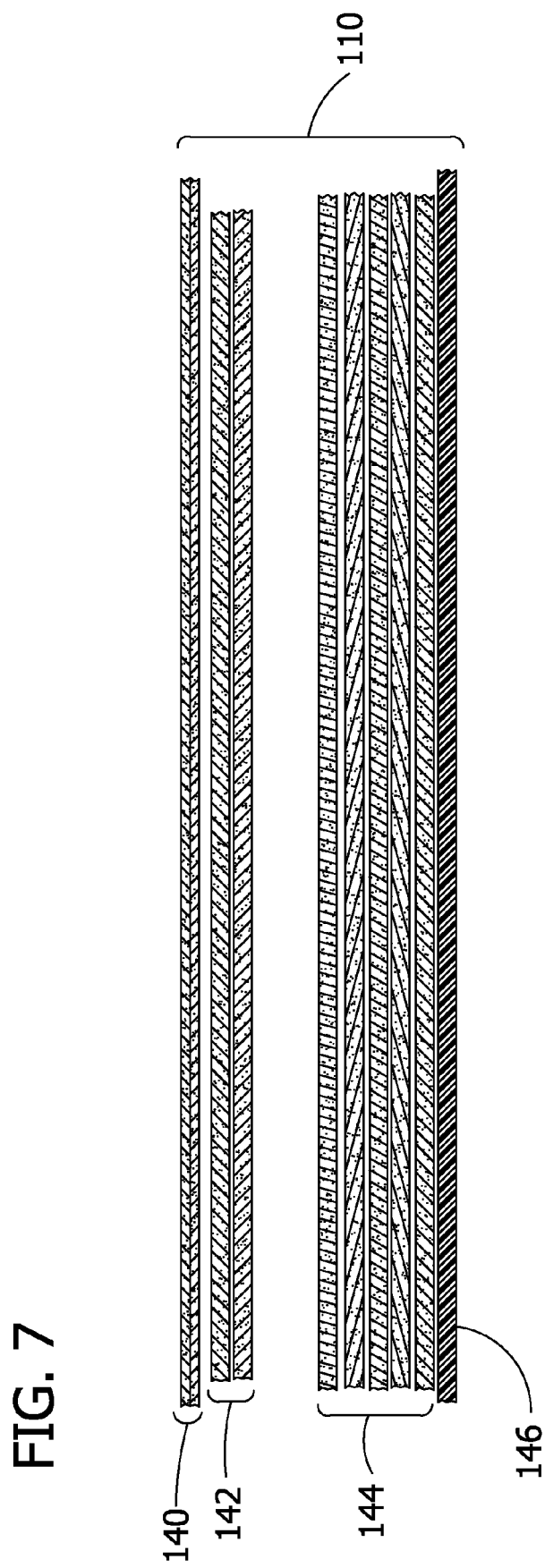
FIG. 7 is a sectional view similar to FIG. 3, but showing another embodiment of making multiple microlayered film subsystems for assembly into a unitary microlayered film system.

With reference to FIG. 7, it will be seen that microlayered film subsystem units may be formed by the coextrusion process, and these subsystem units are then joined to form a unified multiple microlayered film system 110 of the invention. It will be understood that various elastics and fasteners could be connected to the unified system 110 to form a completed diaper (or other absorbent article). In FIG. 7, the intake region 140 (which may include multiple layers) and the uptake and distribution region 142 can be coextruded as a subsystem unit; and another subsystem unit can be coextruded using the retention region 144 alone or in combination with the outer barrier region 146. The invention is not limited to any number of regions or subsystem units of microlayered film that may be used to form the diaper 10.

In general, the product (e.g., diaper 10) comprising the corrugated microlayer film of the present invention may be stretched (e.g., while in use by the wearer) in the machine direction, in the cross direction or in both directions up to about 50% elongation and may retract to about its original length after the removal of the extension force. In another embodiment, the diaper 10 (or other product incorporating the corrugated microlayer film of the present invention) may have extensibility in the machine direction, in the cross direction or in both directions of up to about 100% elongation and may retract to about its original length after the removal of an extension force. The films of the present invention, and hence the diaper 10 into which they are incorporated, also have an increased void volume and significantly reduced bulk density resulting from the microlayer corrugations and void spaces between corrugated microlayers.

Although the present invention contemplates that the intake region 40, uptake and distribution region 42, retention region 44 and barrier region 46 are all made of microlayer material, it is also contemplated that a diaper (not shown) may be made of microlayer material, but with one or more of the regions being made completely or partially out of non-microlayer material. For example, one or more of the regions could be made of conventional diaper materials.

It is possible to combine microlayer material with other material within a given region. For example, a retention region of a diaper (not shown) may include in addition to microlayer structure, a conventional superabsorbent/wood fluff pulp absorbent material. U.S. Pat. No. 6,383,960 entitled LAYERED ABSORBENT STRUCTURE, issued May 7, 2002 and incorporated by reference herein, is exemplary of a superabsorbent/wood fluff pulp absorbent material. A retention region might be formed by microlayer structure of the type disclosed herein in combination with a high superabsorbent-containing structure such as taught in U.S. Pat. No. 5,593,399 entitled ABSORBENT ARTICLE WHICH INCLUDES SUPERABSORBENT MATERIAL LOCATED IN DISCRETE, ELONGATE POCKETS PLACED IN SELECTED PATTERNS, issued Jan. 14, 1997 and incorporated by reference herein. A retention region could in another embodiment have microlayer structure in combination with a softened pulp sheet, such as that disclosed in U.S. Pat. No. 5,562,645, ARTICLE WITH SOFT ABSORBENT PULP SHEET, issued Oct. 8, 1996 and incorporated by reference herein. Regardless of the particular type of ancillary absorbent combined with the microlayer structure, the microlayer structure may be positioned on the body-side of the ancillary absorbent, or distal from the body-side of the ancillary absorbent, or interposed between two layers of the ancillary absorbent. Other geometric arrangements include having the ancillary absorbent interposed between layers of microlayer structures. In some of these embodiments, additional conventional nonwovens or tissue materials may be required to complete the absorbent article.

Figure 8:
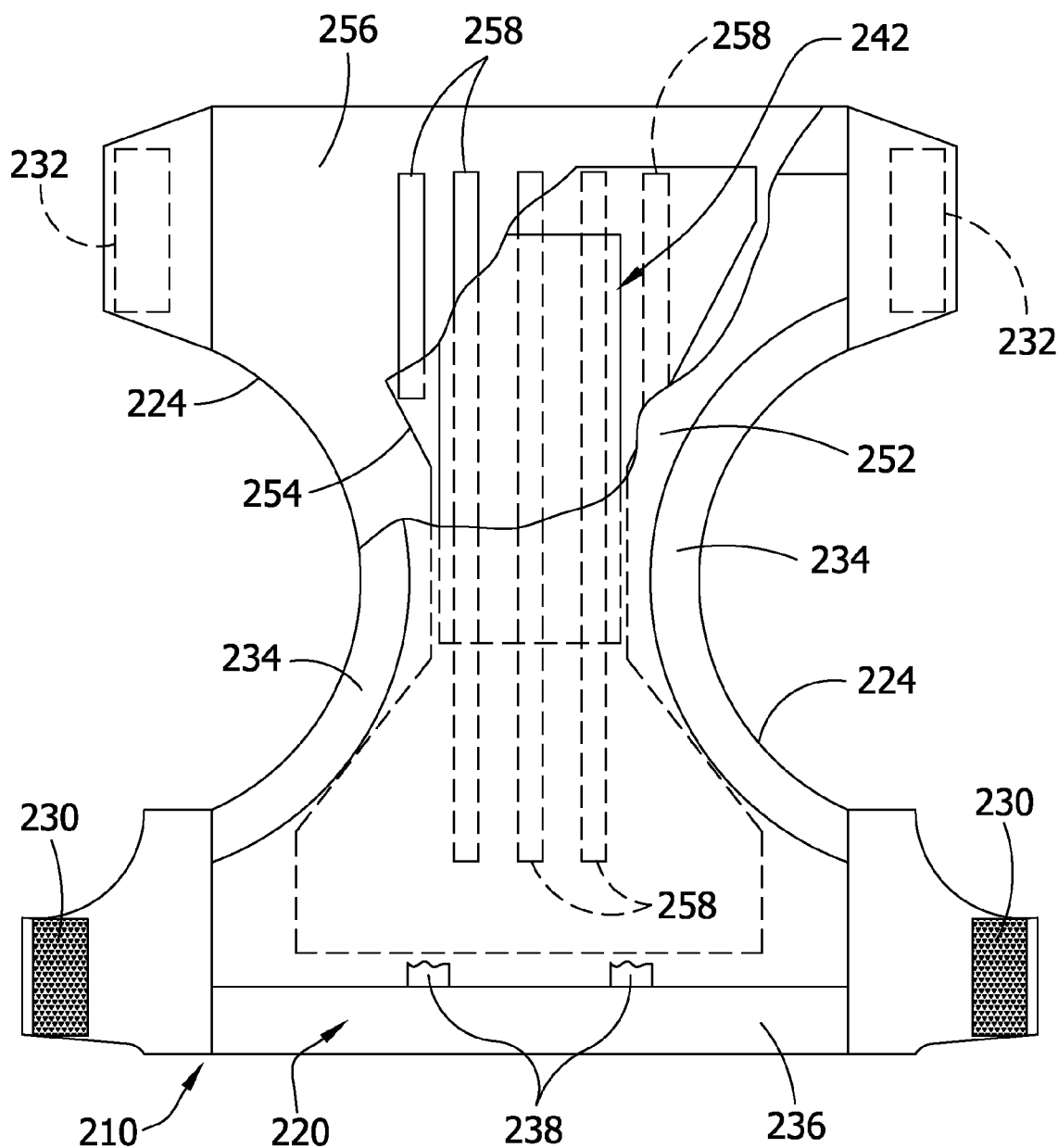
FIG. 8 is a top plan view of a representative absorbent article similar to FIG. 2, but broken away to show a microlayered film system of a different embodiment of the invention.

Another embodiment of the present invention is shown in FIG. 8 in the form of a diaper 210. The diaper 210 has a construction that is substantially the same as the diaper 10 shown in FIG. 2. Corresponding parts of the diaper 210 are indicated by the same reference numerals as diaper 10, plus "200". A bodyside liner 252 of the diaper 210 which contacts the wearer faces upwardly and is partially broken away in FIG. 8. The outer edges of the diaper 210 define a periphery with longitudinally extending side edge margins 224 and laterally extending end edge margins 226. The side edges 224 will define leg openings for the diaper 210, in use. The diaper typically also has a system of elastomeric gathering members, including leg elastics or cuffs 234 to hold the diaper 210 closely around the legs and a waist elastic 236 to draw the diaper around the waist. In addition, other elasticized containment flaps 38 (mostly broken away in FIG. 8) may be provided to extend generally lengthwise in the machine-direction of the diaper 210. The diaper has a suitable fastening system including a first fastener component in the form of fastener tabs 230 on the back ears of the back waistband portion and a second fastener component in the form of landing zone patches 232 on the front ears of a front waistband portion to hold the diaper 210 snugly in place on a wearer so that the back portion overlaps the front portion. The landing zone patches 232 provide a target area for releasable and re-attachable securement with the fastener tabs 230. The description of the diaper 210 thus far is closely the same as for diaper 10 of FIGS. 1 and 2. It is to be understood that variations and differences of construction of the diaper 210 are contemplated.

The diaper 210 differs from the diaper 10 of FIG. 2 in one respect because it has a conventional nonwoven body-side liner 252 (i.e., not made of microlayer material). A first microlayer structure 242 providing surge capacity and liquid distribution is located next to and below the body-side liner 252. Underneath the first microlayer structure 242 is a conventional superabsorbent/wood fluff pulp absorbent core 254 which performs the primary liquid retention function of the diaper 210. Interposed between an outer cover 256 and the superabsorbent/wood fluff pulp absorbent core 254 are several additional microlayer structures in the form of strips 258. In one embodiment, each of the additional microlayer strips are less than or equal to about 3 cm wide and about 30 cm long. The microlayer strips are generally aligned with the longitudinal (machine direction) axis of the diaper. The strips may have other dimensions without departing from the scope of the present invention. The microlayer structure of the strips 258 may include channels (not shown) of a size selected to induce wicking of liquid. For instance, these channels may be smaller in size than those of the first microlayer structure 242. The strips 258 help to handle any liquid that moves past or through the absorbent core 254 to capture and distribute the liquid for absorption by the core.

From the foregoing description it will be seen that the objects and advantages of the invention are met. This disclosure is intended to cover changes and modifications in the multiple microlayered film system invention that will be apparent to those skilled in the art, and is only limited by the scope of the appended claims.

The invention claimed is:

1. An absorbent article comprising a liquid permeable intake region, a liquid retention region which performs the primary liquid retention function of the absorbent article, a liquid impermeable barrier region, and a plurality of strips comprising a microlayer structure located between the liquid retention region and the liquid impermeable barrier region, the strips being configured to distribute liquid that moves through the liquid retention region for absorption by the liquid retention region.

2. An absorbent article as set forth in claim 1 wherein the strips are spaced apart from each other in a lateral direction of the absorbent article.

3. An absorbent article as set forth in claim 1 further comprising a liquid uptake and distribution region located generally between the liquid intake region and the liquid retention region.

4. An absorbent article as set forth in claim 1 wherein the liquid retention region comprises an absorbent core of superabsorbent material and cellulose fibers.

5. An absorbent article as set forth in claim 1 wherein the liquid permeable intake region is a nonwoven body-side liner.

6. An absorbent article as set forth in claim 1 further comprising a microlayer structure providing surge capacity and liquid distribution, the microlayer structure being located adjacent the liquid permeable intake region.

7. An absorbent article as set forth in claim 1 wherein each of the strips of the plurality of strips comprises channels for distributing liquid for absorption by the liquid retention region.

8. An absorbent article as set forth in claim 1 wherein each of the strips of the plurality of strips is aligned with a longitudinal axis of the absorbent article.

9. An absorbent article as set forth in claim 1 wherein each of the strips of the plurality of strips has a width that is less than or equal to about 3 centimeters.

* * * * *

UNITED STATES PATENT AND TRADEMARK OFFICE
CERTIFICATE OF CORRECTION

| | | |
|---|---|---|
| PATENT NO. | : 8,317,767 B2 | Page 1 of 1 |
| APPLICATION NO. | : 11/622277 | |
| DATED | : November 27, 2012 | |
| INVENTOR(S) | : Vukos et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 911 days.

Signed and Sealed this
Twenty-third Day of September, 2014

Michelle K. Lee
*Deputy Director of the United States Patent and Trademark Office*